United States Patent
Patil et al.

(10) Patent No.: US 10,919,846 B2
(45) Date of Patent: Feb. 16, 2021

(54) UREA PRODUCTION PROCESS AND PLANT WITH HEAT INTEGRATION IN LOW PRESSURE RECOVERY SECTION

(71) Applicant: Stamicarbon B.V., Sittard (NL)

(72) Inventors: Rahul Patil, Maastricht (NL); Fredericus Henricus Maria Buitink, Grathem (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 16/961,319

(22) PCT Filed: Dec. 18, 2019

(86) PCT No.: PCT/NL2019/050851
§ 371 (c)(1),
(2) Date: Jul. 10, 2020

(87) PCT Pub. No.: WO2020/130817
PCT Pub. Date: Jun. 25, 2020

(65) Prior Publication Data
US 2020/0385339 A1    Dec. 10, 2020

(30) Foreign Application Priority Data
Dec. 21, 2018 (EP) .................................. 18215356

(51) Int. Cl.
C07C 273/14  (2006.01)
C07C 273/04  (2006.01)
B01J 3/04     (2006.01)
B01D 5/00     (2006.01)
B01D 3/06     (2006.01)
B01D 3/00     (2006.01)

(52) U.S. Cl.
CPC ............ *C07C 273/14* (2013.01); *B01D 3/009* (2013.01); *B01D 3/06* (2013.01); *B01D 5/0003* (2013.01); *B01D 5/006* (2013.01); *B01J 3/04* (2013.01); *C07C 273/04* (2013.01)

(58) Field of Classification Search
None
See application file for complete search history.

(56) References Cited

U.S. PATENT DOCUMENTS 5,359,140 A * 10/1994 Granelli ................ C07C 273/04
564/66
5,767,313 A    6/1998 Jonckers
(Continued)

FOREIGN PATENT DOCUMENTS

GB        1 542 371        3/1979

OTHER PUBLICATIONS

Jozef H. Meessen et al., "Ullmann's Encyclopaedia, chapter Urea", Wiley-VCH Verlag GmbG & Co. GHaA, Weinheim, pp. 1-39, Oct. 2010.
(Continued)

*Primary Examiner* — Tam M Nguyen
(74) *Attorney, Agent, or Firm* — Leason Ellis LLP (57) ABSTRACT

The invention pertains to a urea production process using a high pressure stripper and a low pressure decomposer connected to a low pressure carbamate condenser which is in heat exchanging contact through a wall with a sub-atmospheric decomposer wherein urea solution obtained from the low pressure decomposer is processed.

14 Claims, 2 Drawing Sheets

(56) References Cited

U.S. PATENT DOCUMENTS

| | | | | |
|---|---|---|---|---|
| 5,849,952 A * | 12/1998 | Carloni | ................ | C07C 273/04 |
| | | | | 564/71 |
| 6,231,827 B1 * | 5/2001 | Pagani | ................ | C01O 1/0488 |
| | | | | 423/359 |
| 6,680,407 B2 | 1/2004 | Mennen | | |
| 2009/0124830 A1 * | 5/2009 | Zardi | ................ | C07C 273/04 |
| | | | | 564/70 |
| 2010/0063321 A1 * | 3/2010 | Zardi | ................ | C07C 273/04 |
| | | | | 564/71 |
| 2012/0302789 A1 | 11/2012 | Mennen | | |
| 2014/0081046 A1 * | 3/2014 | Carlessi | ................ | C07C 273/04 |
| | | | | 564/71 |
| 2015/0086440 A1 | 3/2015 | Scheerder | | |
| 2015/0119603 A1 | 4/2015 | Van Den Tillaart et al. | | |
| 2018/0258034 A1 | 9/2018 | Sato et al. | | |
| 2018/0354895 A1 * | 12/2018 | Puci | ................ | B01D 53/1493 |
| 2019/0015811 A1 * | 1/2019 | Coloma Gonz Lez | ................ | |
| | | | | C07C 273/04 |
| 2019/0210963 A1 * | 7/2019 | Mostert | ................ | C07C 273/04 |
| 2019/0359558 A1 * | 11/2019 | Rugnone | ................ | C01O 1/024 |

OTHER PUBLICATIONS

Stamicarbon B.V., "Launch Melt: Ultra Low Energy Design", Brochure, Feb. 13, 2018.

\* cited by examiner

FIG. 4

UREA PRODUCTION PROCESS AND PLANT WITH HEAT INTEGRATION IN LOW PRESSURE RECOVERY SECTION

CROSS-REFERENCE TO RELATED PATENT APPLICATIONS

This application is a U.S. National Phase Application under 35 U.S.C. § 371 of International Patent Application No. PCT/NL2019/050851, filed Dec. 18, 2019, which claims the priority of European Application No. 18215356.9, filed Dec. 21, 2018, all of which are incorporated by reference, as if expressly set forth in their respective entireties herein.

INTRODUCTION

The invention pertains to a urea production process and plant of the stripping type, and to a method of modifying an existing urea plant.

Urea processes with a high pressure stripper and without a high pressure stripper are known. In a urea process without a high pressure stripper, heat supplied to the urea synthesis solution is typically used only once; therefore, this type of process can be referred to as an N=1 process. In urea processes using high pressure stripping, heat is imported in the first heater (the stripper), recovered in the high pressure carbamate condenser, and re-used in low pressure heaters. The heat supplied is effectively used twice; thus the term "N=2 process" is used. The average energy consumption of the stripping process is 0.8-1.0 ton of steam per ton of urea.

In an example typical urea process of the Stamicarbon $CO_2$ stripping type, gas from the low pressure decomposer is passed through a rectifying column (for counter-current contact with incoming urea solution), and then is supplied directly to a low pressure carbamate condenser which uses cooling water. Urea solution from the low pressure decomposer is supplied to a flash vessel and then to a pre-evaporator where it is heated (Ullmann's Encyclopaedia, chapter Urea, 2010).

In Ullmann's Encyclopaedia, chapter Urea, 2010, it is mentioned that in the 1980's, some processes were described that aim at a greater reduction of energy consumption by further application of a multiple effect to N=3, wherein heat supplied to the first heater (the stripper) is effectively used three times (N=3). In particular, in conceptual form, urea synthesis solution is converted into a urea melt by passage through three heaters in series, the second heater using heat of condensation of a condenser for the gas from the first heater; the third heater using heat of condensation provided by a condenser used for condensing gas from the second heater.

US 2015/0119603 describes a method for the production of urea from ammonia and carbon dioxide in a urea plant containing a high-pressure synthesis section with a horizontal pool condenser is provided. The method comprises exchanging heat from a high pressure process medium received in a shell section of the pool condenser to a medium pressure urea containing solution received in a first heat exchanging section provided in the pool condenser to at least decompose ammonium carbamate into $NH_3$ and $CO_2$. In an embodiment, gas produced in the first heat exchanging section is fed to a medium pressure condenser evaporator where the gas is at least partially condensed and wherein water from a urea-water mixture is evaporated under vacuum conditions. It can be seen that heat is effectively used three times in the process of US 2015/0119603.

A disadvantage of US 2015/0119603 is that the first heat exchanger section, e.g. a U-shaped tube bundle, is contact with process medium on both sides. The process medium contains ammonium carbamate and is highly corrosive at the temperatures associated with high pressure and medium pressure operation. This makes it difficult to construct the horizontal pool condenser, in particular the tube-to-tubesheet connection, taking into account that the corrosive fluid in the tubes passes through the bore holes in the tubesheet, which tubesheet consist of carbon steel sandwiched with two corrosion-resistant liners.

US 2015/0086440 describes a method for assembling a tube-sheet and U-shaped tube heat exchanger involving the use of sleeves inserted into the tubesheet; the sleeves are of corrosion resistant duplex stainless steel.

The brochure "Launch Melt Ultra Low Energy Design" on www.stamicarbon.com mentions that by direct heat integration between the high pressure condenser and the medium pressure rectifying heater, followed by direct heat exchange between the medium pressure condenser and the first-stage evaporator heater, the steam intake of the urea plant is minimized to unprecedented lower levels, of less than 600 kg steam per ton of urea produced. In this document, 'direct' heat exchange and 'direct heat integration' refers to heat exchange between separate streams through a wall without the use of a heat transfer fluid.

US 2018/0258034 describes a urea manufacturing method wherein in an embodiment feed ammonia is heated using steam generated by the heat of condensation of the decomposed gas.

US 2012/0302789 describes a urea production process wherein urea solution from the stripper is subjected to adiabatic expansion and separation of vapor and liquid before the liquid enters a first recovery section. The vapor can be condensed and the heat of condensation thereby released can be used for concentrating urea solution.

An object of the present invention is to provide an energy efficient urea production process and plant with a simple design of the high pressure section.

SUMMARY

The invention relates in a first aspect to a urea production process comprising:
A) subjecting ammonia and carbon dioxide to urea-forming conditions in a high pressure reaction zone thereby forming a first urea solution which also comprises carbamate,
B) subjecting the first urea solution to high pressure stripping to decompose carbamate using heat, thereby forming a gas stream and a second urea solution also containing carbamate, and subjecting said gas stream to condensation in a high pressure carbamate condenser, thereby forming a first carbamate-containing solution and releasing heat of condensation, wherein the carbamate-containing solution is supplied to the high pressure reaction zone,
C) subjecting said second urea solution to low pressure carbamate decomposition, or first processing said second urea solution at medium pressure and subjecting the processed second urea solution to low pressure decomposition, wherein said low pressure carbamate decomposition involves heating in a low pressure decomposer the urea solution containing carbamate using said heat of condensation from the high pressure carbamate condenser to decompose carbamate, thereby giving a first vapor and a third urea solution also containing carbamate, and expanding the third urea solution to a sub-atmospheric pressure thereby obtaining an expanded third urea solution, D) subjecting said first vapor to condensation in a first low pressure carbamate condenser, thereby obtaining a second carbamate-containing solution and second vapor and releasing additional heat of condensation, wherein the first low pressure carbamate condenser has an outlet for the second carbamate-containing solution in liquid communication with an inlet of the high pressure reaction zone, and subjecting said expanded third urea solution to decomposition of carbamate in a sub-atmospheric decomposer using said additional heat of condensation from said first low pressure carbamate condenser by heat transfer through a heat-exchanging wall between said first low pressure carbamate condenser and said sub-atmospheric decomposer, thereby obtaining a fourth urea solution and a third vapor, and E) subjecting said third vapor to condensation in a sub-atmospheric carbamate condenser, in indirect heat exchange with cooling fluid, thereby obtaining a fourth carbamate-containing solution.

In a further aspect the invention pertains to a urea plant comprising:

A) a high pressure reaction zone for subjecting ammonia and carbon dioxide to urea-forming conditions thereby forming a first urea solution which also comprises carbamate, B) a high pressure stripper for subjecting the first urea solution to high pressure stripping to decompose carbamate using heat, thereby forming a gas stream and a second urea solution also containing carbamate, and high pressure carbamate condenser for subjecting said gas stream to condensation thereby forming a first carbamate-containing solution and releasing heat of condensation, C) a low pressure decomposer, wherein the low pressure decomposer is configured for subjecting said second urea solution to low pressure decomposition, or wherein the plant is configured for first processing at least a part second urea solution at medium pressure in a medium pressure section to give a processed second urea solution and the low pressure decomposer is configured for subjecting said processed second urea solution to low pressure decomposition, and wherein said low pressure carbamate decomposition involves heating the urea solution containing carbamate using said heat of condensation from the high pressure carbamate condenser to decompose carbamate, thereby giving a first vapor and a third urea solution also containing carbamate, and an expansion system for expanding the third urea solution to a sub-atmospheric pressure thereby obtaining an expanded third urea solution, D) a first low pressure carbamate condenser for subjecting said first vapor to condensation thereby obtaining a second carbamate-containing solution and second vapor and releasing additional heat of condensation, wherein the first low pressure carbamate condenser has an outlet for the second carbamate-containing solution in liquid communication with the high pressure reaction zone, and a sub-atmospheric decomposer for subjecting said expanded third urea solution to decomposition of carbamate using said additional heat of condensation from said first low pressure carbamate condenser by heat transfer through a heat-exchanging wall between said first low pressure carbamate condenser and said sub-atmospheric decomposer, thereby obtaining a fourth urea solution and a third vapor, and E) a sub-atmospheric carbamate condenser configured for subjecting said third vapor to condensation in indirect heat exchange with a cooling fluid, thereby obtaining a fourth carbamate-containing solution, and preferably having an outlet for all or part of the fourth carbamate-containing solution in liquid communication with an inlet of the high pressure reaction zone.

DETAILED DESCRIPTION

The present application is broadly based on the judicious insight to supply, in a urea process of the type with a high pressure stripper, the gas from the decomposer of the low pressure recovery section to two condensers in series, and to use the heat of condensation released in the upstream condenser of said two condensers for a sub-atmospheric decomposition of carbamate in urea solution obtained from the low pressure decomposer.

In this way, heat is used firstly in the high pressure stripper (S) and is released in the high pressure carbamate condenser (HPCC), the heat from the high pressure carbamate condenser is used for a second time in the low pressure (LP) decomposer (LPD) for carbamate decomposition and is released in the upstream first LP carbamate condenser (LPC1) which is used for partial condensation of the gas from the LP decomposer, and the heat released in the first LP carbamate condenser is used for a third time for decomposing carbamate in the urea solution obtained from the low pressure decomposer (LPD) in a sub-atmospheric (LLP) decomposer (LLPD) by heat exchange through a wall between the first LP carbamate condenser and the sub-atmospheric decomposer, hence without a heat transfer fluid to transport heat from LPC1 to LLPD. This provides for good heat integration in the low pressure recovery section. In addition some water is evaporated from the urea solution in the sub-atmospheric decomposer (LLPD).

Accordingly, the first LP carbamate condenser (LPC1) is heat integrated with the sub-atmospheric decomposer (LLPD) by heat exchange through a wall rather than using a heat transfer fluid between these units. The use of such sub-atmospheric decomposer is preferably combined with carrying out the high pressure striping at lower stripping efficiency α (alfa) of the high pressure stripper, e.g. with stripping efficiency α of less than 75%, more preferably 60-70%, and preferably using $CO_2$ as strip gas, compared to a stripping efficiency α of more than 78% in a known urea process of the $CO_2$ stripping type.

In a preferred embodiment, the HP stripper is operated with a stripping efficiency (α) of 75% or less, for example 50%-75% or preferably 60-70%, for example 63-68% wherein the stripper preferably uses $CO_2$ as strip gas.

Accordingly the high pressure stripping with the lower stripping efficiency (e.g. α of less than 75%) requires significantly less heat, i.e. provides for a much lower steam consumption. In addition, the high pressure stripping involves lower temperatures and this reduces hydrolysis of urea in the stripper compared to stripping at higher stripping efficiency. The reduced hydrolysis provides effectively for a conversion increase or at least a urea yield increase. Accordingly, the flow of feed ($CO_2$ and $NH_3$, in kg/h) can be reduced (for same urea production in kg/h), which provides for a longer residence time (for a fixed reaction zone volume). This further increases the urea conversion (or urea yield). In an example embodiment, in total about 7% to about 10% extra urea production capacity can be achieved (based on constant reaction zone volume), or alternatively the reaction zone can be 7%-10% by volume smaller with the same urea production capacity. The reaction zone is often a reactor of urea grade steel, which is an expensive construction material.

Furthermore with the lower stripping efficiency, the heat exchange duty (condensation duty) of the HPCC is reduced, e.g. with more than 25%, such as reduced with 30 to 40%, which can provide for a smaller heat exchanging surface area (e.g. smaller tube bundle) or, in case of a fixed heat exchanging surface area, for an increase in the pressure of the steam raised in the HPCC, e.g. a 1 bar pressure increase, which makes the steam more useful for further use.

In addition, utilizing the heat of condensation released in LPC1 for separation of $NH_3$, $CO_2$, and water from urea containing stream (under sub-atmospheric conditions) in LLPD provide for an advantageously low heat exchanger wall temperature (for wall LPHX) due to lower temperature difference. This provides for reduced biuret formation. The heat exchanger wall temperature is in particular lower than if a typical heat transfer fluid is used, such as LP Steam at about 4.5 bar absolute. In the same way, the heat exchanging wall of the wall MPHX in the optional embodiment with a medium pressure carbamate condenser MPC can be lower than if LP steam is used for pre-evaporation.

A lower stripping efficiency advantageously also provides for reduced biuret formation over the stripper.

The overall effect of utilizing the carbamate heat of condensation at LPC1 and the preferred MPC along with lower stripping efficiency is quantified as decrease in biuret by 0.04 wt. % to 0.06 wt. % in the final product.

The vapor from the sub-atmospheric decomposer is condensed in a sub-atmospheric condenser (LLPC), resulting in a carbamate-containing solution, which comprises water, carbamate, and some urea (e.g. 35-45 wt. % carbamate, rest mainly water and about 0.5-2% (e.g. wt. %) entrained urea). In preferred embodiments of the invention, this carbamate containing solution is supplied partially or entirely to ultimately the high pressure reaction zone, preferably entirely, even though it has a high water fraction (e.g. at least 40 wt. % water, for instance 65-55 wt. % water). The somewhat higher water recycle to the reaction zone is balanced with the advantage of the greatly reduced steam consumption, in particular for high pressure stripping. The sub-atmospheric decomposer ensures sufficient purification of the urea solution even with a lower degree of high pressure stripping. In preferred embodiments, the carbamate-containing solution from LLPC is supplied in part or entirely, preferably entirely, indirectly to an inlet of the high pressure reaction zone, e.g. by first supplying the carbamate-containing solution, containing e.g. at least 50 wt. % water, to another carbamate condenser where the water fraction is advantageously used to avoid crystallization of carbamate.

In contradistinction, in known urea production plants, aqueous streams containing a small amount of ammonia and urea (or correspondingly containing a large part water), which streams are obtained e.g. by the condensers of the vacuum evaporation section, are typically sent to a waste water treatment section for purification. The purification may e.g. involve desorbing (to remove ammonia) and hydrolysis (to remove urea). The purification is highly energy intensive (has a high steam consumption), in particular for the hydrolyser. Hence it is advantageous that the condensate from the LLPC can be recycled entirely to the HP synthesis reaction zone, thereby not increasing the load on any waste water treatment section while still achieving good conversion.

The presence of urea in the condensate from the LLPC is considered to be mainly or completely due to physical entrainment in the droplets from LLPD in the vapor stream, without wishing to be bound by way of theory.

In an optional embodiment, a part or all of the carbamate-containing solution, e.g. the condensate, from the LPCC is processed in a desorber column or in a waste water treatment section, for instance a fraction of 10-90 wt. % of the condensate, and for instance by dividing the condensate in a part supplied ultimately to the high pressure reaction zone and a part supplied to a desorber column or waste water treatment section. The processing of the condensate in the desorber and/or waste water treatment section gives two streams, a purified condensate (e.g. essentially pure water) as first stream, which purified condensate is typically not reintroduced into the process streams in the high pressure reaction zone. The second stream is typically a carbamate-containing solution with more than 10 wt. % carbamate, and is e.g. recycled to the high pressure reaction zone.

The vapor (non-condensed gases including $NH_3$ and $CO_2$) in the first LP carbamate condenser is optionally condensed in the second downstream LP carbamate condenser (LPC2), which uses cooling water; the condensate (carbamate-containing solution) is recycled to the urea synthesis reaction zone; in some other embodiments the vapor is vented instead after optional scrubbing. In a first preferred embodiment, the carbamate-containing solution from the LPC2 is supplied to the LPC1, because water supply is often necessary in LPC1 so as to avoid crystallization of carbamate in LPC1. In a second preferred embodiment, the carbamate-containing solution from LPC1 is supplied to LPC2, and the carbamate-containing solution from LLPC is supplied to LPC1. In this embodiment, in particular vapor (V2) and liquid (C2) are supplied, e.g. as mixture, from LPC1 to LPC2 for further condensation of the vapors (V2) against cooling fluid (e.g. cooling water), in the presence of liquid (C2) received from LPC1. The carbamate-containing solution (C2) from LPC2 is for instance supplied to the high pressure synthesis section, in particular recycled back to the HP reaction zone. In this way the carbamate (C4) from LLPC provides first the necessary water supply to LPC1 so as to avoid crystallization of carbamate in LPC1. The liquid (C2) from LPC1 supplied to LPC2 provides the necessary water supply to LPC2. This second preferred embodiment is less preferred than the first preferred embodiment in terms of energy benefits, but still provides significant energy benefits compared to existing urea processes with $CO_2$ stripping.

Preferably, the urea solution from the stripper is expanded to medium pressure (MP) and is subjected to medium pressure processing before it is expanded to low pressure and supplied to the LP decomposer. More preferably, the medium pressure processing is an adiabatic flash, to give flashed urea solution and medium pressure vapor. Alternatively, the medium pressure processing is medium pressure decomposition giving processed urea solution and medium pressure vapor. The medium pressure decomposition can involve heating; the heat used therein can for instance be supplied as steam, for example from the HPCC. The heat can for example also be supplied by heat exchange through a wall with the condensing medium in the HPCC, more in particular, in case the HPCC is a shell-and-tube heat exchanger comprising a tube bundle, by supplying the medium pressure urea solution through the tubes of the HPCC while the high pressure process medium is present on the shell side and condenses on the shell side, thereby releasing heat. For both types of preferred MP processing, the MP flash and the MP decomposition, the MP vapor is preferably condensed in a MP condenser (MPC), which preferably also receives carbamate-containing solution from LPC1 and/or from the optional LPC2 (which solutions include some water), so as to avoid crystallization of carbamate. The resulting carbamate-containing solution is pumped and supplied to the high pressure reaction zone, for instance through the high pressure carbamate condenser. The heat of condensation released in the MP condenser is preferably used for evaporating water from the urea solution from the sub-atmospheric decomposer, by heat exchange through a wall.

Very advantageously, no special design of the high pressure section is required (for grassroots plants), likewise no special modifications of the high pressure section are necessary (for revamps of existing urea plants). The additional equipment such as the heat exchanging vessel for LPC1/LLPD is low pressure equipment, optionally with additional medium pressure equipment such as a heat exchanging vessel MPC/PEV, and hence operates at lower temperatures at which carbamate is less corrosive. This greatly reduces equipment costs compared to high pressure equipment, for instance because there is no need to use special corrosion resistant materials such as duplex stainless steel alloys.

The inventive urea production process comprises subjecting ammonia and carbon dioxide to urea-forming conditions in a high pressure reaction zone (R) thereby forming a first urea solution (U1) which also comprises carbamate. The process further comprises subjecting the first urea solution to high pressure stripping (S) to decompose carbamate using heat (H1, S1), thereby forming a gas stream (SG) and a second urea solution (U2) also containing carbamate, and subjecting the gas stream (SG) to condensation in a high pressure carbamate condenser (HPCC), thereby forming a first carbamate-containing solution (C1) and releasing heat of condensation (H2, S2), wherein the carbamate-containing solution (C1) is supplied to the high pressure reaction zone.

The process further comprises subjecting the second urea solution (U2) to low pressure carbamate decomposition, or first processing said second urea solution (U2) at medium pressure (MPP) and subjecting the processed second urea solution (U2a) to low pressure decomposition. The low pressure carbamate decomposition involves heating in a low pressure decomposer (LPD) the urea solution (U2, U2a) containing carbamate using said heat of condensation (H2, S2) from the high pressure carbamate condenser to decompose carbamate, thereby giving a first vapor (V1) and a third urea solution (U3) also containing carbamate, and expanding the third urea solution to a sub-atmospheric pressure (F1, X1) thereby obtaining an expanded third urea solution (U3a).

The process further comprises subjecting the first vapor (V1) to condensation in a first low pressure carbamate condenser (LPC1), thereby obtaining a second carbamate-containing solution (C2) and second vapor (V2) and releasing additional heat of condensation (H3). The first low pressure carbamate condenser has an outlet for the second carbamate-containing solution (C2) in liquid communication with an inlet of the high pressure reaction zone (R).

The process further comprises subjecting said expanded third urea solution (U3a) to decomposition of carbamate in a sub-atmospheric decomposer (LLPD) using said additional heat of condensation (H3) from said first low pressure carbamate condenser (LPC1) by heat transfer through a heat-exchanging wall (LPHX) between said first low pressure carbamate condenser (LPC1) and said sub-atmospheric decomposer (LLPD), thereby obtaining a fourth urea solution (U4) and a third vapor (V3). The process further comprises subjecting said third vapor (V3) to condensation in a sub-atmospheric carbamate condenser (LLPC), in indirect heat exchange with cooling fluid, thereby obtaining a fourth carbamate-containing solution (C4).

The process optionally further comprises subjecting the second vapor (V2) to condensation in a second low pressure carbamate condenser (LPC2), in indirect heat exchange with cooling fluid (CW), thereby obtaining a third carbamate-containing solution (C3), wherein the second low pressure carbamate condenser (LPC2) has an outlet for the third carbamate-containing solution (C3) in liquid communication with an inlet of the high pressure reaction zone (R). In some embodiments the second vapor (V2) is vented instead optionally after scrubbing.

In a preferred embodiment, the sub-atmospheric carbamate condenser (LLPC) has an outlet for at least part of the fourth carbamate-containing solution (C4) in liquid communication with the high pressure reaction zone (R).

The urea plant (UP) of the invention comprises a high pressure reaction zone (R) for subjecting ammonia and carbon dioxide to urea-forming conditions thereby forming a first urea solution (U1) which also comprises carbamate; and a high pressure stripper (S) for subjecting the first urea solution to high pressure stripping to decompose carbamate using heat (H1, S1), thereby forming a gas stream (SG) and a second urea solution (U2) also containing carbamate, and high pressure carbamate condenser (HPCC) for subjecting said gas stream (SG) to condensation thereby forming a first carbamate-containing solution (C1) and releasing heat of condensation (H2, S2).

The urea plant further comprises a low pressure decomposer (LPD). The low pressure decomposer (LPD) is configured for subjecting said second urea solution (U2) to low pressure decomposition, or the plant is configured for first processing at least a part second urea solution (U2) at medium pressure (MPP) in a medium pressure section (MPP) to give a processed second urea solution and the low pressure decomposer (LPD) is configured for subjecting said processed second urea solution to low pressure decomposition. The low pressure carbamate decomposition involves heating the urea solution containing carbamate using said heat of condensation (H2, S2) from the high pressure carbamate condenser to decompose carbamate, thereby giving a first vapor (V1) and a third urea solution (U3) also containing carbamate. The urea plant further comprises an expansion system (F1, X1) for expanding the third urea solution to a sub-atmospheric pressure thereby obtaining an expanded third urea solution (U3a). The urea plant further comprises a first low pressure carbamate condenser (LPC1) for subjecting said first vapor (V1) to condensation thereby obtaining a second carbamate-containing solution (C2) and second vapor (V2) and releasing additional heat of condensation (H3). The first low pressure carbamate condenser (LPC1) has an outlet for the second carbamate-containing solution (C2) in liquid communication with the high pressure reaction zone (R).

The urea plant further comprises a sub-atmospheric decomposer (LLPD) for subjecting said expanded third urea solution (U3a) to decomposition of carbamate using said additional heat of condensation (H3) from said first low pressure carbamate condenser (LPC1) by heat transfer through a heat-exchanging wall (LPHX) between said first low pressure carbamate condenser (LPC1) and said sub-atmospheric decomposer (LLPD), thereby obtaining a fourth urea solution (U4) and a third vapor (V3).

The urea plant further comprises a sub-atmospheric carbamate condenser (LLPC) which is configured for subjecting said third vapor (V3) to condensation in indirect heat exchange with a cooling fluid, thereby obtaining a fourth carbamate-containing solution (C4), and which preferably has an outlet for all or part of the fourth carbamate-containing solution (C4) in liquid communication with an inlet of the high pressure reaction zone (R).

Figure 1:
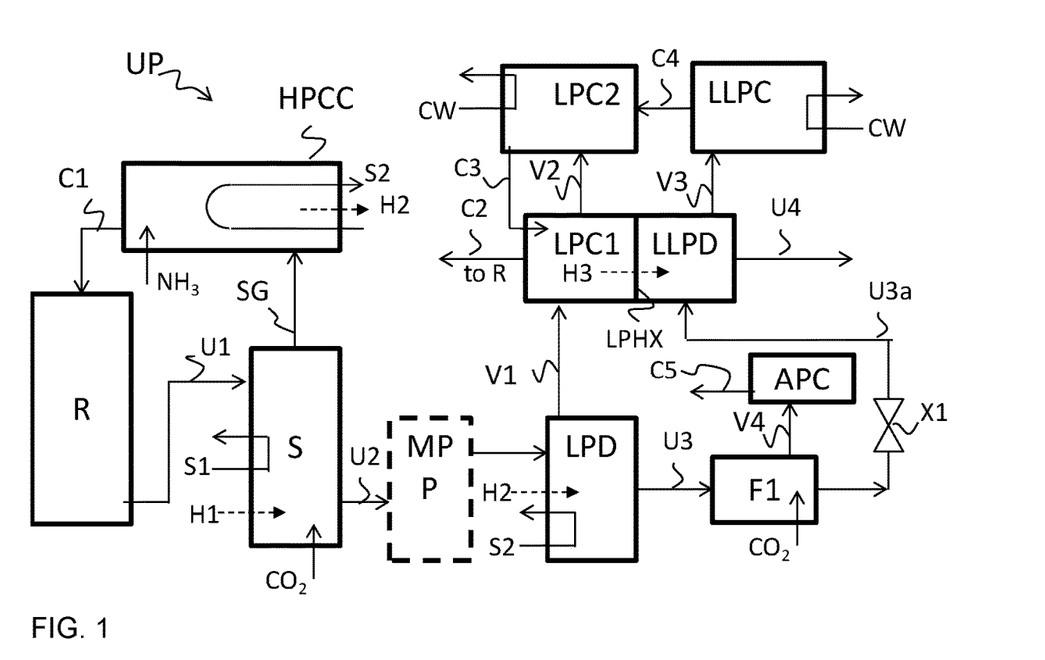
FIG. 1 shows a process scheme of an example embodiment according to the invention.

The invention pertains to a urea production process and a urea plant which is preferably configured for this process. An example process and plant is illustrated in FIG. 1.

The urea plant (UP) comprises a HP synthesis section comprising a HP reaction zone (R), a HP stripper (S) and a HP carbamate condenser (HPLC). The HP reaction zone (R) is configured for subjecting ammonia and carbon dioxide to urea-forming conditions thereby forming a first urea solution (U1) which also comprises carbamate (ammonium carbamate), and typically also comprises water and ammonia. The process involves subjecting ammonia and carbon dioxide to urea-forming conditions in a HP reaction zone (R) thereby forming the first urea solution (U1). The reaction is performed e.g. with an N/C, ratio of 2.5 to 3.5, preferably 3.0-3.2. The N/C ratio is the molar ratio of $NH_3$ to $CO_2$ in the reaction zone based on the theoretical initial mixture.

The HP stripper (S) is configured for subjecting the first urea solution (U1) (urea synthesis solution) to high pressure stripping to decompose a part of the carbamate into $NH_3$ and $CO_2$ using heat (H1), in particular using a first steam (S1), thereby forming a gas stream (SG) (e.g. mixed gas) which comprises $NH_3$ and $CO_2$, and second urea solution (U2) (stripped urea solution) also containing carbamate, ammonia and water. The HP stripper uses e.g. $CO_2$ as strip gas in a urea plant of the $CO_2$ stripping plant as is illustrated in FIG. 1. Ammonia stripping and self-stripping can also be used; in combination with $CO_2$ feed supply to the reaction zone (R). The high pressure stripping typically involves counter-current contact between incoming first urea solution and a gas stream having a lower vapor pressure for $NH_3$ or $CO_2$ than the first urea solution.

In a preferred embodiment, the first urea solution (U1) has an N/C ratio of about 3 (e.g. 2.5-3.5), and the stripped urea solution urea solution (U2) at the outlet of the stripper has an N/C ratio of 2.0-2.3, optionally from 2.10 to 2.30.

The first steam (S1) is for example extracted from a steam turbine of a $CO_2$ feed compressor of the urea plant. The first steam is for instance and is typically taken from a utility plant, e.g. a dedicated boiling system using fossil fuels, optionally through a steam turbine, or is for instance taken from an upstream ammonia plant, or is for example saturated steam (e.g. 18 to 20 bara) received from any plant.

The HP carbamate condenser (HPCC) comprises a process medium side and a coolant fluid side and a heat exchanging wall between these sides, and is configured for subjecting said gas stream (SG) to condensation of carbamate thereby forming a first carbamate-containing solution (C1) on the process medium side. This condensation of carbamate involves release of heat of condensation (H2), preferably by raising a second steam (S2) on the coolant fluid side. The high pressure carbamate condenser (HPCC) has a connection for supplying the first carbamate-containing solution (C1) to the high pressure reaction zone (R). The urea plant is configured for supplying the first carbamate-containing solution (C1) from the high pressure carbamate condenser (HPCC) to the high pressure reaction zone, optionally using a connection between separate vessels or involving transport of solution within a combined vessel. The process involves supplying the carbamate-containing solution (C1) to the high pressure reaction zone.

The method involves supplying $NH_3$ feed to the HP reaction zone, optionally through the HPCC. Already some urea may be formed in the high pressure carbamate condenser, e.g. more than 10 wt. %, more than 30 wt. % and/or less than 90 wt. % of the total urea formed in the process. Accordingly the HP reaction zone is in some embodiments provided at least in part in the HP carbamate condenser. The HP carbamate condenser is for instance heat exchanger using cooling water as cooling liquid, e.g. a shell-and-tube heat exchanger, for example with a U-shaped tube bundle and for instance with cooling water in the tubes and process medium in the shell side.

The urea plant may comprise one or more HP reaction zones. The or at least one HP reaction zone is in some embodiments a reactor, e.g. a vertical reactor, which is a separate vessel from the HP carbamate condenser. In some embodiment the HP reaction zone and the HP carbamate condenser can be provided by separate vessels. In some embodiments, the HP reaction zone or at least one of the HP reaction zones and the HP carbamate condenser are combined in a single vessel, the single vessel is preferably a vessel with a horizontal submerged condenser part; optionally the plant comprises a further HP reaction zone downstream of the vessel, e.g. as vertical reactor. The condenser in in such combined vessel is for instance a shell-and-tube heat exchanger with a tube bundle. The tube bundle can be e.g. a U-shaped tube bundle or a straight tube bundle. In operation cooling fluid is typically supplied through the tubes and the gas stream (SG) from the stripper is supplied to the shell section. The vessel is for instance in a pool reactor as described in U.S. Pat. No. 5,767,313 or a vertical combination reactor as described in U.S. Pat. No. 6,680,407.

The HP equipment, e.g. the reactor, stripper and HP carbamate condenser, is for instance made of a corrosion resistant material such as urea grade steel e.g. ferritic-austenitic duplex stainless steel, for at least the parts in contact with the process medium.

The urea plant comprises a connection between an outlet of the HP reaction zone to an inlet of the HP stripper for first urea solution, a connection between an outlet of the stripper and an inlet of the HP carbamate condenser for the gas stream (SG), and in some embodiments a connection between an outlet of the HP carbamate condenser and an inlet of the HP reaction zone for the first carbamate solution. The stripper preferably has an inlet for strip gas and the HP carbamate condenser preferably has an inlet for ammonia feed.

In some embodiments, the urea plant comprises a HP scrubber for scrubbing gases from an outlet of the HP synthesis section, e.g. from HPCC. These gases are in particular inerts (e.g. passivation air, if used). In the preferred embodiments with a medium pressure condenser, the urea plant preferably does not comprise a HP scrubber.

The urea plant furthermore comprises a low pressure recovery section receiving at least part, for example all, of the second urea solution (U2) from the stripper, and optionally a medium pressure section (MPP) between the stripper and the low pressure recovery section for processing at least a part of, optionally all of, the second urea solution (U2) to give a processed second urea solution (U2a).

The urea plant, in particular the LP recovery section, comprises a low pressure decomposer (LPD). The low pressure decomposer (LPD) is configured for subjecting the second urea solution (U2) and/or processed second urea solution (U2a) to carbamate decomposition at low pressure and has an inlet for these streams with a connection to the outlet of the stripper and/or a connection to an outlet of the medium pressure section (MPP). The LP decomposition involves heating the optionally processed second urea solution containing carbamate (U2, U2a) using the heat of condensation (H2), from the HP carbamate condenser to decompose carbamate, preferably by heat exchange with the second steam (S2), thereby giving a first vapor (V1) which comprises $CO_2$ and $NH_3$ as well as water vapor, and a third urea solution (U3) also containing carbamate and water.

The LP decomposer comprises for instance a rectifying column for contact between the incoming (optionally processed) second urea solution containing carbamate (U2, U2a) and the first vapor (V1), in particular for counter-current contact between these streams. The rectifying column is used for instance to reduce the water content of the first vapor (V1). The rectifying column comprises for instance a packing and has for instance a heat exchanger zone for heat exchange with steam at the bottom.

In a preferred embodiment, a part of the $CO_2$ feed is supplied to the atmospheric flash (F1) to adjust the N/C ratio of the first vapor (V1), to have a desirable lower N/C ratio for better condensation of the first vapor (V1). In a preferred embodiment, the adiabatic flash vessel (F1) is configured for counter-current contact between the gaseous $CO_2$ stream and the urea solution, thereby stripping a part of the $NH_3$ species in the urea solution, preferably adiabatically. Preferably the flash vessel (F1) comprises a packed bed for this contacting.

In a preferred embodiment, the flash vessel (F1) is an atmospheric pressure stripper. In a preferred embodiment, a part of the $CO_2$ feed, is supplied to the atmospheric flash (F1), wherein said part is in an amount of e.g. the 1 to 10 wt. %, more preferably 3 to 8 wt. % of the total $CO_2$ feed to the urea plant. In a preferred embodiment, the stripping effect of the $CO_2$ supplied to the atmospheric flash provides for a reduction of the N/C ratio from about 4.0 at the inlet for urea solution (U3) to about 2.6 at the outlet for urea solution (U3a). The N/C correction in the flash vessel provides the advantage that the condensation temperature in LLPC is sufficiently high (e.g. above 30° C.) to be utilize typical available cooling water (e.g. 30-40° C.) in LLPC for carbamate condensation at sub-atmospheric pressure.

The plant, in particular the low pressure recovery section, further comprises an expansion system (F1, X1) for expanding the third urea solution (U3) to a sub-atmospheric pressure (less than 1.0 bar absolute, e.g. 0.10-0.9 bara, preferably 0.3-0.5 bara), thereby obtaining an expanded third urea solution (U3a). The process further comprises such expansion.

In an preferred embodiment, the expansion system comprises a atmospheric flash vessel (F1) having an inlet for the third urea solution (U3), for expanding the urea solution to atmospheric pressure (e.g. 1 to 2 bar absolute, for instance 1.0 to 1.8 bara or preferably 1.0-1.3 bara), for instance with adiabatic flashing, giving a fourth vapor (V4) and a urea solution, and an expansion valve (X1) for expanding the urea solution further to a sub-atmospheric pressure to give the expanded third urea solution (U3a). The process preferably further comprises condensing the fourth vapor (V4) in an atmospheric pressure condenser (APC) to give a fifth carbamate-containing solution (C5). The atmospheric pressure condenser (APC) has an outlet for the fifth carbamate-containing solution (C5) which is in indirect liquid connection with the high pressure reactor (R) to effect recycle of the carbamate. Preferably, the process comprises supplying the fifth carbamate-containing solution (C5) to the first and/or second low pressure carbamate condenser (LPC1, LPC2). In this way the water fraction of the fifth carbamate-containing solution (C5) elegantly is used for avoiding crystallization of carbamate in the first and/or second low pressure carbamate condenser (LPC1, LPC2).

The low pressure recovery section further comprises a first low pressure carbamate condenser (LPC1) for subjecting the first vapor (V1) to condensation of carbamate, thereby obtaining a second carbamate-containing solution (C2) and a second vapor (V2) and releasing additional heat of condensation (H3). The condensation is partial. The first low pressure carbamate condenser (LPC1) has an inlet with a connection to an outlet for the first vapor (V1) of the low pressure decomposer. The LPC1 operating pressure is preferably 6-9 bara, more preferably it is 8 bara; these pressures provide for an optimum condensation temperature in LPC1 for heat integration with LLPD.

The first low pressure carbamate condenser (LPC1) has an outlet for the second carbamate-containing solution (C2) in liquid communication with the high pressure reaction zone (R). Hence, the process comprises indirectly supplying the second carbamate-containing solution (C2) to the high pressure reaction zone (R), optionally through the second LP carbamate condenser, and for instance through the HP carbamate condenser and using a pump. In this way the process comprises a recycle of the carbamate to the HP synthesis section.

The urea plant furthermore comprises a sub-atmospheric decomposer (LLPD) that is configured for subjecting said expanded third urea solution (U3a) to decomposition of carbamate, using the additional heat of condensation (H3) from the first low pressure carbamate condenser (LPC1), thereby obtaining a fourth urea solution (U4) and a third vapor (V3). The sub-atmospheric decomposer (LLPD) has an inlet with a connection to an outlet for expanded third urea solution (U3a) of the expansion system and has an outlet for the fourth urea solution (U4) and an outlet for the third vapor (V3).

The urea plant comprises a heat-exchanging wall (LPHX) between said first low pressure carbamate condenser (LPC1) and said sub-atmospheric decomposer (LLPD). Hence, in practice the low pressure carbamate condenser (LPC1) and said sub-atmospheric decomposer (LLPD) are combined in a single vessel, more in particular in a heat exchanger, e.g. in a shell-and-tube heat exchanger, with the expanded third urea solution (U3a) on a first side (e.g. the tube side) and the first vapor (V1) on a second side of the heat exchanger (e.g. the shell side), separated for mass transport by the heat-exchanging wall (LPHX). The single vessel is preferably configured a counter-current shell-and-tube heat exchanger with tubes and a shell side, which is more preferably configured a submerged condenser on the shell side (LPC1) with the tubes submerged in the liquid phase in the shell side, and with falling film evaporation in the tubes (LPD1), and with flow in the tubes counter-current to the flow in the shell side.

The process involves heat transfer through this heat-exchanging wall (LPHX). The fourth urea solution (U4)

preferably comprises at least 60 wt. % urea, more preferably at least 70 wt. % urea, e.g. 70 to 80 wt. % urea, for instance 70 to 76 wt. % urea.

The urea plant further comprises a second low pressure carbamate condenser (LPC2) that is configured for subjecting said second vapor (V2) to condensation of in indirect heat exchange, typically with a cooling fluid such as cooling water (CW), thereby obtaining a third carbamate-containing solution (C3).

The second low pressure carbamate condenser (LPC2) has an inlet connected with an outlet for second vapor (V2) of the first low pressure carbamate condenser (LPC1), and has an outlet for the third carbamate-containing solution (C3) in liquid communication with an inlet of the HP reaction zone (R), to supply the third carbamate-containing solution (C3) ultimately to the HP reaction zone (R), typically through the HP carbamate condenser and using a pump. The second low pressure carbamate condenser (LPC2) is for instance a shell-and-tube heat exchanger.

In an optional embodiment, LPC2 can be omitted. With appropriate operating conditions for the LPC1/LLPD unit and with the heat integration between LPC1 and LLPD, LPC2 can have very low to no heat duty (heat duty for cooling against cooling water). Hence in an optional embodiment, LPC2 is omitted.

In such an embodiment, the carbamate solution (C4) from the sub-atmospheric condenser (LLPC) is supplied e.g. to the first LP condenser (LPC1) and the vapor (V2) from the first LP condenser (LPC1) is vented optionally after scrubbing.

The urea plant further comprises a sub-atmospheric carbamate condenser (LLPC) that is configured for subjecting the third vapor (V3) to condensation of carbamate in indirect heat exchange with a cooling fluid (CW), thereby obtaining a fourth carbamate-containing solution (C4). The sub-atmospheric carbamate condenser (LLPC) has an inlet for the third vapor (V3) with a connection to the outlet for third vapor (V3) of the sub-atmospheric decomposer (LLPD), and has an outlet for the fourth carbamate-containing solution (C4).

The fourth carbamate-containing solution (C4) comprises e.g. at least 20 wt. % carbamate and e.g. less than 70 wt. % carbamate, e.g. 30-50 wt. % carbamate, typically with rest essentially water.

The outlet for the sub-atmospheric carbamate condenser (LLPC) is preferably for all or part of the fourth carbamate-containing solution (C4) and is preferably in liquid communication with an inlet of the high pressure reaction zone (R). Optimally the sub-atmospheric carbamate condenser (LLPC) has an outlet for all or part of the fourth carbamate-containing solution (C4) in liquid communication with an inlet of a desorber column and/or waste water treatment section. The process preferably involves supplying all or part of the fourth carbamate-containing solution (C4) indirectly to the high pressure reaction zone (R), preferably through the first and/or second low pressure carbamate condenser (LPC1, LPC2) and then through the HP carbamate condenser. The sub-atmospheric carbamate condenser (LLPC) is preferably a shell-and-tube heat exchange with condensation on the shell side and cooling water in the tubes; further preferably a horizontal surface condenser, with a horizontal tube bundle and with condensation on the surface of the tubes, or further preferably a vertical falling film condenser with a vertical tube bundle. Preferably the tubes are provided as straight tube bundle. Preferably the tubes are provided with stainless steel material on both sides (inner and outer surface of the tube wall) since the tubes are on both side exposed to process medium comprising carbamate. In a particularly preferred embodiment, a straight tube bundle with 316L steel on the shell side (outer tube surface) and 304L steel on the tube side (inner tube surface) is used.

In a preferred embodiment, the sub-atmospheric carbamate condenser (LLPC) has an outlet for at least part of the fourth carbamate-containing solution (C4) which is in liquid communication with the high pressure reaction zone (R), preferably through the first and/or second low pressure carbamate condenser (LPC1, LPC2) and optionally through the HP carbamate condenser (HPCC). In an optional embodiment wherein the urea plant does not contain a medium pressure condenser, the fourth carbamate-containing solution is preferably supplied to a HP scrubber of the urea plant, wherein the HP scrubber has an outlet for carbamate-solution connected to an inlet of the HP carbamate condenser.

In a preferred embodiment, the third carbamate-containing solution (C3) is supplied to the first low pressure carbamate condenser (LPC1), and the fourth carbamate-containing solution (C4) is supplied to the second low pressure carbamate condenser (LPC2); and the plant accordingly comprises a connection between an outlet of LPC2 to an inlet of LPC1 for the third carbamate-containing solution (C3) and a connection from an outlet of the LLPC to an inlet of LPC2 for the fourth carbamate-containing solution (C4). The second carbamate-containing solution (C2) is supplied to the HP reaction zone. This provides for an energy efficient urea production process and plant.

FIG. 1 shows a process scheme of an example of such an embodiment, wherein furthermore the stripper is a $CO_2$ stripper, and the preferred atmospheric condenser (APC) is used. Optionally the medium pressure processing unit (MPP) is used. A part of the $CO_2$ feed is used for N/C correction in the atmospheric flash (F1). Furthermore expansion valves (not shown) are included for each expansion/pressure reduction step, such as between the HP stripper and the low pressure decomposer. In addition, pumps and/or ejectors are included (not shown) for the pressure increase of liquid streams, such as in stream C4 from LLPC to LPC. Furthermore LLPC, LPC2 and MPC typically have outlets for non-condensed vapors (in particular, inerts, e.g. from optionally used passivation air and/or from traces of hydrogen and/or $N_2$ from the $CO_2$ feed and/or $NH_3$ feed). The HP carbamate condenser HPCC in some embodiments has an outlet for gas connected to a HP scrubber or MP scrubber; in other embodiments the HP synthesis section does not include a HP scrubber. These outlets are not shown in FIG. 1. Furthermore the arrows for heat (H1, H2, H3) indicate conceptual heat flows rather than process streams; the same applies for heat flow H4 in FIG. 3.

In another embodiment, the second carbamate-containing solution (C2) is supplied from an outlet of the first low pressure carbamate condenser (LPC1) to an inlet of the second low pressure carbamate condenser (LPC2) and the fourth carbamate-containing solution (C4) is supplied from the an outlet of the sub-atmospheric carbamate condenser (LLPC) to an inlet of the first low pressure carbamate condenser (LPC1); and the plant comprises the connections between these inlets and outlets.

Figure 2:
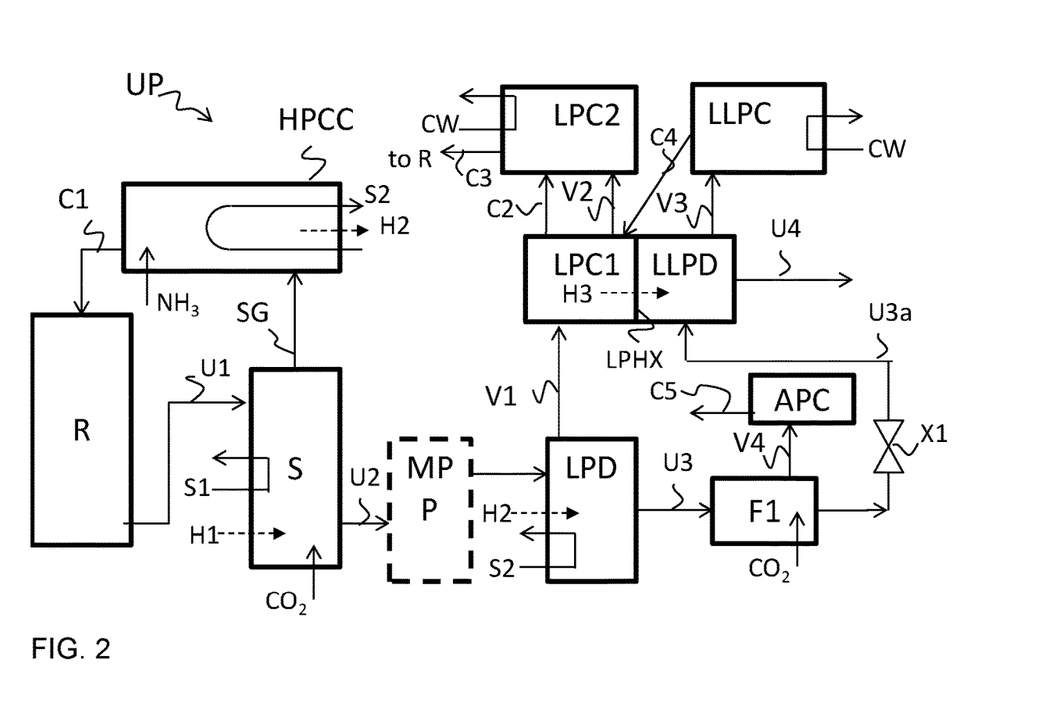
FIG. 2 shows a process scheme of an example embodiment according to the invention.

FIG. 2 schematically illustrates an example of such an embodiment wherein solution C4 is supplied from LLPC to LPC2, which embodiment is less preferred than the embodiment in FIG. 1.

The first low pressure carbamate condenser (LPC1) and the second low pressure carbamate condenser (LPC2) are, each independently, preferably a submerged condenser with liquid as the continuous phase, and is for instance a shell-and-tube heat exchanger, preferably with cooling fluid in the tubes; preferably both the first and second low pressure carbamate condenser are such condensers. The first low pressure carbamate condenser (LPC1) is a combined unit with the sub-atmospheric decomposer (LLPD) and this combined unit is preferably a shell-and-tube heat exchanger with a tube bundle and with condensation of the vapor (V1) in the shell side and heating of the urea solution (U3a) in the tubes, more preferably configured as submerged condenser. Preferably the heating of the urea solution uses falling-film evaporation in the tubes, alternatively rising film evaporation can be used in the tubes; further preferably the tubes are on the shell side submerged in the liquid phase of carbamate-containing solution, alternatively falling film condensation can for example be used on the shell side. The tube bundle is preferably vertical.

The first low pressure carbamate condenser (LPC1) is preferably operated at a higher temperature than the second low pressure carbamate condenser (LPC2), e.g. at a temperature at least 10° C. or at least 20° C. higher. LPC1 is preferably used for partial condensation of the vapor, with LPC2 being used for condensing remaining $CO_2$ and $NH_3$ in vapor V2 to carbamate. In some embodiments, LPC1 and LPC2 are integrated into a single shell.

The LP recovery section comprises for example the units LPD, LPC1, LPC2, F1, APC, LLPD and LLPC; even though F1, APC, LLPD and LLPC operate at a pressure lower than 2 bar absolute.

In a preferred embodiment, the processes comprises first processing said second urea solution (U2) at medium pressure (MPP) and subjecting the processed second urea solution (U2a) to the low pressure carbamate decomposition (LPD). The medium pressure processing preferably involves removing ammonia and/or carbamate from the urea solution, and the processing gives a processed second urea solution (U2a) also containing carbamate and a fifth vapor (V5) containing $NH_3$ and $CO_2$, for instance 60 wt. % $CO_2$, 5 wt. % water and rest $NH_3$. The pressure reduction of the stripped urea solution (U2) to medium pressure provides for carbamate decomposition.

The process preferably comprises condensing the fifth in a medium pressure condenser (MPC) giving a sixth carbamate-containing solution (C6). Preferably the second carbamate-containing solution (C2) from said first low pressure carbamate condenser (LPC1) and/or the third carbamate-containing solution (C3) from the sub-atmospheric carbamate condenser (LLPC) are supplied the medium pressure condenser (MPC) and the plant comprises connections between inlets and outlets for such flows. Preferably the medium pressure condenser (MPC) has an outlet for the sixth carbamate-containing solution (C6) in liquid communication with an inlet of the high pressure reaction zone (R), and preferably the process involves supplying the sixth carbamate-containing solution (C6) directly or indirectly to the high pressure reaction zone (R).

Figure 3:
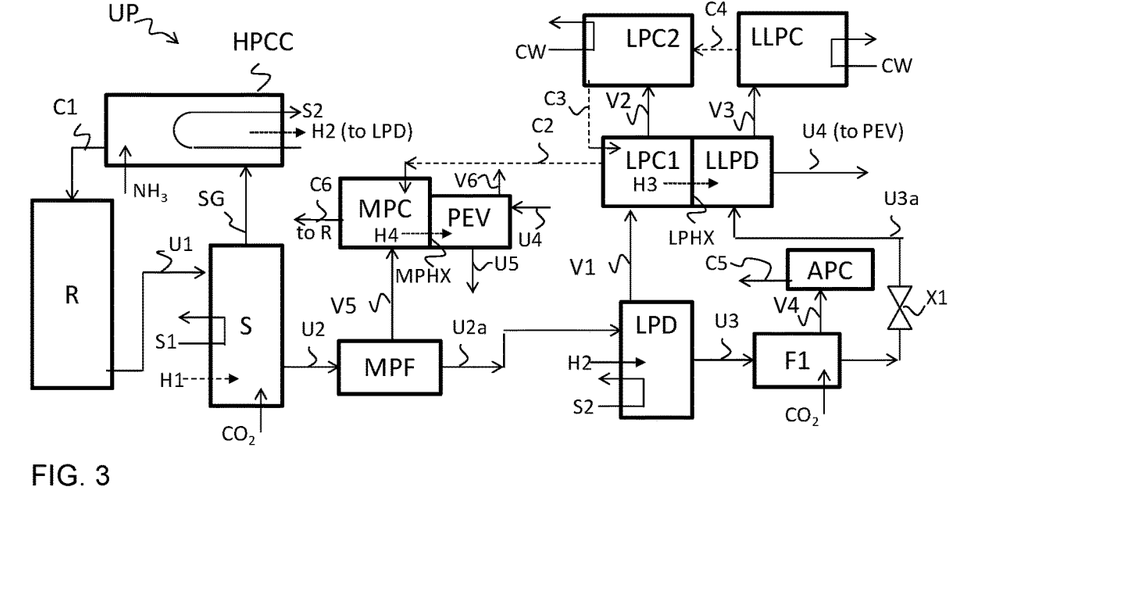
FIG. 3 shows a process scheme of an example embodiment according to the invention.

Preferably the method further comprises heating the fourth urea solution (U4) from the sub-atmospheric carbamate condenser (LLPD) (optionally through a urea storage tank) in a pre-evaporator (PEV) to evaporate water from the urea solution, optionally also decomposing some remaining carbamate, using the heat of condensation (H4) that is released by the carbamate condensation in said medium pressure condenser (MPC), thereby giving a fifth urea solution (U5) with reduced water content and a sixth vapor (V6) which is mainly water vapor. The sixth vapor is e.g. condensed and the condensate is e.g. sent to a waste water treatment section. The fifth urea solution (U5) comprises e.g. at least 80 wt. % urea, preferably at least 85 wt. % urea, for instance 86-95 wt. % urea, for example 93 wt. % urea. An example process according to this embodiment is illustrated in FIG. 3.

Preferably, the medium pressure carbamate condenser (MPC) is a combined vessel with the pre-evaporator (PEV) and is more preferably a shell-and-tube heat exchanger with a tube bundle and with the condensation of the MP vapor (V5) in the shell side and heating of the urea solution (U4) in the tubes, more preferably configured as submerged condenser. Preferably the heating of the urea solution uses falling-film evaporation in the tubes, alternatively rising film evaporation can be used in the tubes; preferably the tubes are on the shell side submerged in the liquid phase of carbamate-containing solution. Preferably the shell-and-tube heat exchanger is configured for flow in the tubes counter-current to the flow on the shell side such that the vapor inlet is near to the urea solution outlet. The tube bundle of the MPC is preferably vertical.

Preferably, the processing at medium pressure comprises adiabatic flashing of the second urea solution (U2) in a medium pressure flash vessel (MPF), such that the processed urea solution is a flashed second urea solution (U2a). This embodiment is illustrated in FIG. 3.

In combination with the low pressure recovery section according to the invention, a very energy efficient process can advantageously be achieved with adiabatic flashing as the medium pressure processing. Furthermore a medium pressure adiabatic flash vessel is relatively simple equipment.

FIG. 3 schematically illustrates an example embodiment with a medium pressure flash vessel (MPF) for adiabatic flashing of the stripper second urea solution (U2) from the HP stripper. FIG. 3 schematically also shows that in the LP recovery section is as shown in FIG. 1; i.e. solution C2 is supplied from an LPC1 to LPC2 and solution C4 is supplied from LLPC to LPC1; this configuration is independent of the use of MP processing and other configurations are also possible. For instance, a further example urea plant comprises the medium pressure flash vessel (MPF) and the LP recovery section configuration is as shown in FIG. 2.

In another embodiment, the processing at medium pressure comprises heating of the second urea solution (U2) in a medium pressure decomposer, thereby decomposing carbamate. The medium pressure heating uses e.g. steam as heating fluid. In an embodiment, the medium pressure heating involves heat exchange through a wall with condensing high pressure process medium in the HP carbamate condenser; for instance in a HP carbamate condenser having two tube bundles, one for the second urea solution (U2), optionally after a flash, and another for cooling water to raise steam.

The urea-solution (U4) from the sub-atmospheric decomposer (LPD) and/or the urea solution (U5) from the pre-evaporator (PEV) is for example supplied to an evaporation section of the urea plant (UP) which comprises for instance one, two, three or more vacuum evaporation stages in series to evaporate water, giving vapor and a urea melt (with e.g. at least 95 wt. % or at least 99 wt. % urea); the vapor is e.g. condensed and supplied to a waste-water treatment section. The waste-water treatment section (WWT) comprises e.g. a desorber column and a deep hydrolysis unit. The deep hydrolysis typically involves heating using steam, e.g. steam of more than 10 bar, as heating fluid. The cleaned condensate from the WWT is typically not recycled to the HP synthesis section as process medium but is e.g. disposed at battery limit optionally after having been used as cooling fluid. The urea melt is e.g. supplied to a finishing section for solidification into a solid urea product, such as a granulator or prilling tower. The urea solutions can e.g. also be used as liquid, for instance for the production of Diesel Exhaust Fluid (DEF) and/or liquid fertilizer such as urea ammonium nitrate (UAN).

The invention pertains also to a method of modifying an existing urea plant to obtain a plant according to the invention.

In a preferred method of modifying an existing urea plant, the existing LP carbamate condenser becomes the optional second LP carbamate condenser and a heat exchanging vessel for LPC1/LLPD is added, optionally furthermore an MP processing section is added comprising a heat exchanger for MPC/PEV and e.g. an MP flash vessel MPF or a medium pressure decomposer.

For a preferred method of modifying an existing urea plant, the existing urea plant comprises: a high pressure reaction zone (R) for forming a first urea solution (U1) which also comprises carbamate, a high pressure stripper (S) for subjecting the first urea solution to high pressure stripping to decompose carbamate using heat (H1, S1), thereby forming a gas stream (SG) and a second urea solution (U2) also containing carbamate, and a high pressure carbamate condenser (HPCC) for subjecting said gas stream (SG) to condensation thereby forming a first carbamate-containing solution (C1) and releasing heat of condensation (H2, S2), wherein the high pressure carbamate condenser (HPCC) has a connection for supplying carbamate-containing solution (C1) to the high pressure reaction zone. The existing plant further comprises a low pressure decomposer (LPD), wherein the low pressure decomposer (LPD) is configured for subjecting said second urea solution (U2) to low pressure decomposition, or wherein the low pressure decomposer (LPD) is configured for subjecting the processed second urea solution to low pressure carbamate decomposition and wherein the existing plant is configured for first processing said second urea solution (U2) at medium pressure (MPP) in a medium pressure section to give said processed second urea solution. The low pressure carbamate decomposition involves heating in the second urea solution (U2) containing carbamate using said heat of condensation (H2, S2) from the high pressure carbamate condenser to decompose carbamate, thereby giving a first vapor (V1) and a third urea solution (U3) also containing carbamate.

The method comprises adding an existing low pressure carbamate condenser configured for subjecting first vapor (V1) to condensation, and an expansion system (F1, X1) for expanding the third urea solution to a sub-atmospheric pressure thereby obtaining an expanded third urea solution (U3a) if the existing plant does not comprise such an expansion vessel. The method further comprises adding a unit comprising a first low pressure carbamate condenser (LPC1) and a sub-atmospheric decomposer (LLPD), wherein the first low pressure carbamate condenser (LPC1) is configured for subjecting said first vapor (V1) to condensation thereby obtaining a second carbamate-containing solution (C2) and second vapor (V2) and releasing additional heat of condensation (H3), wherein the first low pressure carbamate condenser (LPC1) has an outlet for transport of the second carbamate-containing solution (C2) to the high pressure reaction zone (R), and wherein the sub-atmospheric decomposer (LLPD) is configured for subjecting said expanded third urea solution (U3a) to decomposition of carbamate in using said additional heat of condensation (H3) from said first low pressure carbamate condenser (LPC1) by heat transfer through a heat-exchanging wall (LPHX) between said first low pressure carbamate condenser (LPC1) and said sub-atmospheric decomposer (LLPD), thereby obtaining a fourth urea solution (U4) and a third vapor (V3). The method optionally further comprises modifying the existing low pressure carbamate condenser into a second low pressure carbamate condenser (LPC2), having an inlet for said second vapor (V2) and configured for second vapor (V2) condensation in indirect heat exchange with cooling fluid (CW), thereby obtaining a third carbamate-containing solution (C3), and having an outlet for transport of the third carbamate-containing solution (C3) to the high pressure reaction zone (R). The method further comprises adding a sub-atmospheric carbamate condenser (LLPC) configured for subjecting said third vapor (V3) to condensation in indirect heat exchange with cooling fluid, thereby obtaining a fourth carbamate-containing solution (C4), and having an outlet for transport of part or all of the fourth carbamate-containing solution (C4) to the high pressure reaction zone (R). The modified plant is preferably the inventive plant and is preferably configured for carrying out the inventive urea production process, with preferably the preferred process features and plant features as discussed hereinabove.

Figure 4:
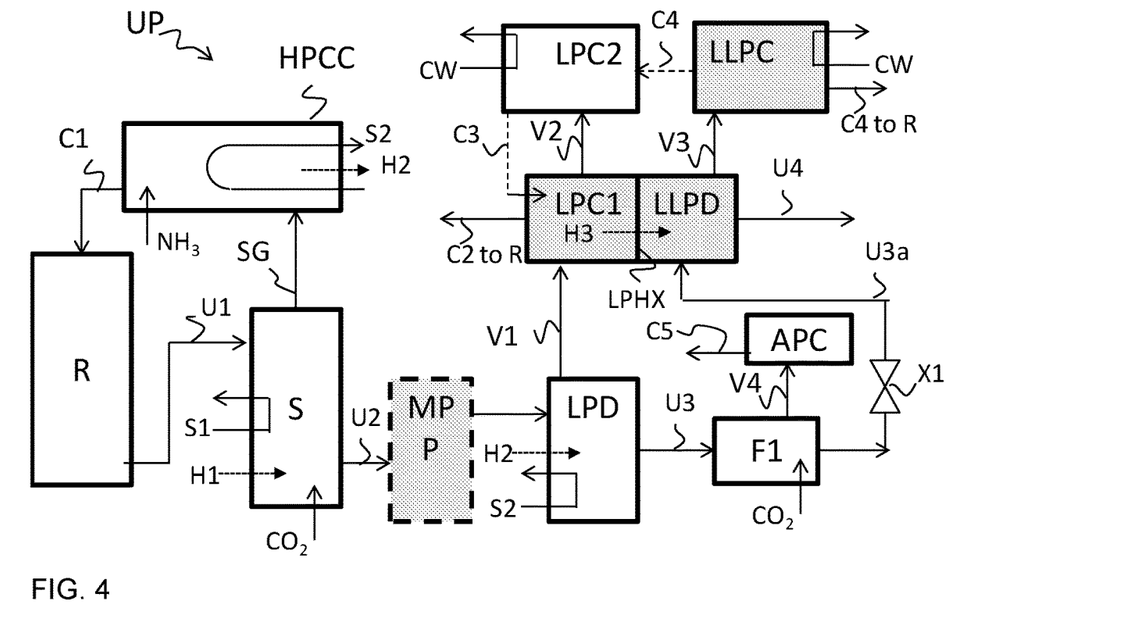
FIG. 4 schematically illustrates an example embodiment of a method according to the invention of modifying an existing plant.

FIG. 4 shows an example of such a method of modifying an existing urea plant. The existing plant comprises the HP synthesis section with the reactor R, stripper S, and HP carbamate condenser HPCC, and a LP recovery section comprising the LP decomposer LPD as well as an existing LP condenser using cooling water CW for the vapor V1 from LPD, for example as a shell-and-tube heat exchanger with a U-shaped tube bundle. A heat exchanging unit providing for the first LP carbamate condenser LPC1 as well as the sub-atmospheric decomposer LLPD is added, for example a vessel as described, preferably a shell-and-tube heat exchanger with a straight tube bundle, as well as the sub-atmospheric carbamate condenser LLPC. The units added in the method are shaded. The existing LP condenser becomes optionally LPC2 receiving vapor V2 from the added unit LPC1. Carbamate solution C4 from LLPC is for example supplied to LPC2 and carbamate solution C3 from LPC2 is for example supplied to LPC1. Alternatively the configuration of FIG. 2 can also be used.

Preferably in the modified plant the atmospheric condenser (APC) has an outlet for the fifth carbamate-containing solution (C5) connected to the second low pressure carbamate condenser (LPC2).

In a further preferred embodiment the method of modifying the plant comprises adding an MP processing section (MPP), preferably an adiabatic flash vessel (MPF) as described.

The process of the invention is preferably carried out in the plant of the invention. The plant of the invention is preferably suitable for the plant of the invention. Preferences discussed in connection with the plant apply also for the process. Preferences discussed in connection with the process apply also for the plant.

As used herein, HP is at least 100 bara, e.g. 110-160 bara, MP is 20-60 bara, LP is 4-10 bara, atmospheric is 1-2 bara, for instance 1.0-1.8 bara and sub-atmospheric (LLP) is less than 1.0 bara, e.g. 0.2-0.5 bara; these pressure ranges are for process solutions and not necessarily the same for steam and heating fluids. The abbreviation "bara" means bar absolute.

The term "liquid communication" refers to a flow line (e.g. tubing or ducts) allowing for passage of liquid between two units, optionally through a number of intermediate units.

Liquid communication does not involve gas phase transport, and hence two units that are connected by an evaporator, a flow line for vapor, and a condenser are not in liquid communication, although they are in fluid communication (which encompasses both gas phase transport and liquid transport). A first unit is in liquid communication with a second unit for instance if the outlet for liquid of the first unit is connected with an inlet of a condenser and an outlet for liquid of the condenser is connected with an inlet of the second unit.

The stripper efficiency (alfa) is defined as the amount of ammonia converted to urea (and biuret) divided by the total amount of ammonia, typically measured at the liquid outlet of the stripper. This definition is equivalent to that of the $NH_3$ conversion based on the outlet of the stripper. Hence, alfa=(2*wt. % urea/60)/((2*wt. % urea/60)+(wt. % $NH_3$/17)), measured at the liquid outlet of the stripper, wherein wt. % $NH_3$ includes all ammonia species including ammonium carbamate. The skilled person understands that "stripping efficiency" refers to the urea purity at the stripper liquid outlet and not to the energy efficiency of the stripper.

Condensation in a carbamate condenser refers to so-called carbamate condensation, which involves the reaction of $NH_3$ and $CO_2$ into ammonium carbamate which is a liquid, such that in effect gaseous $NH_3$ and $CO_2$ become carbamate in a liquid phase. Carbamate decomposition refers to the dissociation reaction of carbamate into $NH_3$ and $CO_2$.

EXAMPLE 1

An example process is carried out with the process scheme of FIG. 3. The HP stripper operates with an example stripping efficiency (alfa) of 0.63 and the stripper has at the outlet the stripped urea solution U1 at 170-180° C. and 140-145 bar (HP) (all pressure are absolute pressure), which is adiabatically flashed in MPF to give a flashed urea solution U2a at 20-30 bar (MP) and 140-150° C. Stream U2a is supplied to the decomposer LPD for decomposition of carbamate which has a rectifying column and gives stream U3 at 5-8 bar (LP) and 130-140° C., which is flashed in flash vessel F1 to 1-1.3 bar and expanded in valve X1 to 0.3-0.5 bar absolute (LLP) at 60-70° C. at the inlet of LLPD. Optionally some fresh $CO_2$ is added to flash vessel F1 for N/C correction. Vapor V3 from LLPD is 70-85° C. and 0.3-0.5 bar. Urea solution U4 at the outlet of LLPD and inlet of PEV is 0.3-0.5 bar and 75-90° C. and is heated to give urea solution U5 at 125-135° C. and 0.3-0.5 bar. Vapor V5 from MPF is 20-30 bar and 140-150° C. and is condensed in MPC to carbamate solution C6 at 20-30 bar and 105-115° C. MPC is a shell-and-tube heat exchanger for counter-current flow in the shell and tubes with gas inlet temperature the shell side of 140-150° C. which is at the same end as the tube outlets for urea solution.

LLPC heats cooling water CW from 32° C. to 35° C., solution C4 at the outlet of LLPC is 0.3-0.5 bar and 35-40° C. and is pumped to LPC2 which gives carbamate solution C3 at 5-8 bar and 75-85° C., heating cooling water CW from 55° C. to 65° C. which is supplied to LPC1. Vapor V2 from LPC1 is 85-95° C. at 5-8 bar. A very low energy consumption of 580-660 kg steam per ton urea product is achieved. Furthermore the heat duty of the HP carbamate condenser is reduced by 37%. With MPF omitted (e.g. as in FIG. 1), still a low energy consumption of 720-800 kg steam per ton urea product is achieved. These steam consumption values are based on steam at 18-23 bara and about 300° C.; it is also possible to use e.g. saturated steam of 18-23 bara. In the example, the stripped urea solution U2 comprises in the example 44 wt. % urea, 15 wt. % $NH_3$, 16 wt. % $CO_2$ and 25 wt. % $H_2O$. Urea solution U5 from PEV has a urea concentration of 86-95 wt. %, preferably 93 wt. %. Urea solution U4 from LLPD has a urea concentration of 70-76 wt. %, preferably 73 wt. %.

The invention claimed is:

1. A urea production process comprising:
   A) subjecting ammonia and carbon dioxide to urea-forming conditions in a high pressure reaction zone thereby forming a first urea solution which also comprises carbamate,
   B) subjecting the first urea solution to high pressure stripping to decompose carbamate using heat, thereby forming a gas stream and a second urea solution also containing carbamate, and subjecting said gas stream to condensation in a high pressure carbamate condenser, thereby forming a first carbamate-containing solution and releasing heat of condensation, wherein the carbamate-containing solution is supplied to the high pressure reaction zone,
   C) subjecting said second urea solution to low pressure carbamate decomposition, or first processing said second urea solution at medium pressure and subjecting the processed second urea solution to low pressure decomposition, wherein said low pressure carbamate decomposition involves heating in a low pressure decomposer the urea solution containing carbamate using said heat of condensation from the high pressure carbamate condenser to decompose carbamate, thereby giving a first vapor and a third urea solution also containing carbamate, and expanding the third urea solution to a sub-atmospheric pressure thereby obtaining an expanded third urea solution,
   D) subjecting said first vapor to condensation in a first low pressure carbamate condenser, thereby obtaining a second carbamate-containing solution and second vapor and releasing additional heat of condensation, wherein the first low pressure carbamate condenser has an outlet for the second carbamate-containing solution in liquid communication with an inlet of the high pressure reaction zone,
   and subjecting said expanded third urea solution to decomposition of carbamate in a sub-atmospheric decomposer using said additional heat of condensation from said first low pressure carbamate condenser by heat transfer through a heat-exchanging wall between said first low pressure carbamate condenser and said sub-atmospheric decomposer, thereby obtaining a fourth urea solution and a third vapor, and
   E) subjecting said third vapor to condensation in a sub-atmospheric carbamate condenser, in indirect heat exchange with cooling fluid, thereby obtaining a fourth carbamate-containing solution.

2. The process of claim 1, wherein the sub-atmospheric carbamate condenser has an outlet for at least part of the fourth carbamate-containing solution in liquid communication with the high pressure reaction zone.

3. The process of claim 1, further comprising:
   subjecting said second vapor to condensation in a second low pressure carbamate condenser, in indirect heat exchange with cooling fluid, thereby obtaining a third carbamate-containing solution, wherein the second low pressure carbamate condenser has an outlet for the third carbamate-containing solution in liquid communication with an inlet of the high pressure reaction zone.

4. The process of claim 1, wherein the expansion of the third urea solution to a sub-atmospheric pressure involves an atmospheric flash giving a fourth vapor and a urea solution which is further expanded to a sub-atmospheric pressure to give the expanded third urea solution, and wherein the process comprises condensing the fourth vapor in an atmospheric pressure condenser to give a fifth carbamate-containing solution, and supplying the fifth carbamate-containing solution to said first and/or second low pressure carbamate condenser and/or to said second low pressure carbamate condenser.

5. The process according to claim 1, wherein the method comprises first processing said second urea solution at medium pressure, wherein said processing gives a processed second urea solution also containing carbamate and a fifth vapor, and condensing said fifth vapor in a medium pressure condenser giving a sixth carbamate-containing solution, wherein said second carbamate-containing solution from said first low pressure carbamate condenser and/or the third carbamate-containing solution from the sub-atmospheric carbamate condenser is supplied to said medium pressure condenser and wherein said medium pressure condenser has an outlet for the sixth carbamate-containing solution in liquid communication with an inlet of the high pressure reaction zone,
    wherein the method further comprises subjecting the processed second urea solution to said low pressure carbamate decomposition, and heating said fourth urea solution in a pre-evaporator to evaporate water using heat of condensation released in said medium pressure condenser thereby giving a fifth urea solution and a sixth vapor.

6. The process according to claim 5, wherein said processing at medium pressure comprises adiabatic flashing of the second urea solution in a medium pressure flash vessel, wherein the processed urea solution is a flashed second urea solution.

7. The process of claim 5, wherein said processing at medium pressure comprises heating of the second urea solution in a medium pressure decomposer, thereby decomposing carbamate.

8. The process of claim 3, wherein the third carbamate-containing solution is supplied to the first low pressure carbamate condenser, and wherein the fourth carbamate-containing solution is supplied to the second low pressure carbamate condenser.

9. The process of claim 3, wherein said second carbamate-containing solution is supplied from said first low pressure carbamate condenser to said second low pressure carbamate condenser and wherein the fourth carbamate-containing solution is supplied to the first low pressure carbamate condenser.

10. The process according to claim 1, wherein the high pressure stripper uses $CO_2$ as strip gas and is operated with a stripping efficiency of 60-70%.

11. A urea plant comprising:
A) a high pressure reaction zone for subjecting ammonia and carbon dioxide to urea-forming conditions thereby forming a first urea solution which also comprises carbamate,
B) a high pressure stripper for subjecting the first urea solution to high pressure stripping to decompose carbamate using heat, thereby forming a gas stream and a second urea solution also containing carbamate,
and high pressure carbamate condenser for subjecting said gas stream to condensation thereby forming a first carbamate-containing solution and releasing heat of condensation,
C) a low pressure decomposer,
    wherein the low pressure decomposer is configured for subjecting said second urea solution to low pressure decomposition, or wherein the plant is configured for first processing at least a part second urea solution at medium pressure in a medium pressure section to give a processed second urea solution and the low pressure decomposer is configured for subjecting said processed second urea solution to low pressure decomposition, and wherein said low pressure carbamate decomposition involves heating the urea solution containing carbamate using said heat of condensation from the high pressure carbamate condenser to decompose carbamate, thereby giving a first vapor and a third urea solution also containing carbamate,
and an expansion system for expanding the third urea solution to a sub-atmospheric pressure thereby obtaining an expanded third urea solution,
D) a first low pressure carbamate condenser for subjecting said first vapor to condensation thereby obtaining a second carbamate-containing solution and second vapor and releasing additional heat of condensation, wherein the first low pressure carbamate condenser has an outlet for the second carbamate-containing solution in liquid communication with the high pressure reaction zone,
and a sub-atmospheric decomposer for subjecting said expanded third urea solution to decomposition of carbamate using said additional heat of condensation from said first low pressure carbamate condenser by heat transfer through a heat-exchanging wall between said first low pressure carbamate condenser and said sub-atmospheric decomposer, thereby obtaining a fourth urea solution and a third vapor, and
E) a sub-atmospheric carbamate condenser configured for subjecting said third vapor to condensation in indirect heat exchange with a cooling fluid, thereby obtaining a fourth carbamate-containing solution, and preferably having an outlet for all or part of the fourth carbamate-containing solution in liquid communication with an inlet of the high pressure reaction zone.

12. A urea plant according to claim 11, further comprising a second low pressure carbamate condenser configured for subjecting said second vapor to condensation of in indirect heat exchange with a cooling fluid, thereby obtaining a third carbamate-containing solution, and having an outlet for the third carbamate-containing solution in liquid communication with an inlet of the high pressure reaction zone.

13. A urea plant according to claim 11, wherein the plant comprises medium pressure processing section for processing said second urea solution at medium pressure, wherein said processing gives a processed second urea solution also containing carbamate and a fifth vapor, wherein said plant further comprises a medium pressure condenser for condensing said fifth vapor to give a sixth carbamate-containing solution, and having an outlet for said second carbamate-containing solution from said first low pressure carbamate condenser and/or an outlet for the third carbamate-containing solution from the sub-atmospheric carbamate condenser connected to said medium pressure condenser and wherein said medium pressure condenser has an outlet for the sixth carbamate-containing solution in liquid communication with an inlet of the high pressure reaction zone, wherein the medium pressure processing section has an outlet for said processed second urea solution connected to said low pressure carbamate decomposition,
    wherein the plant further comprises pre-evaporator for heating said fourth urea solution to evaporate water using heat of condensation released in said medium pressure condenser thereby giving a fifth urea solution and a sixth vapor,
wherein medium pressure-processing section is medium pressure flash vessel for adiabatic flashing of the second urea solution.

14. A method of modifying an existing urea plant, preferably to arrive at the urea plant of claim 11, wherein the existing urea plant comprises:
- A) a high pressure reaction zone for forming a first urea solution which also comprises carbamate,
- B) a high pressure stripper for subjecting the first urea solution to high pressure stripping to decompose carbamate using heat, thereby forming a gas stream and a second urea solution also containing carbamate,
and a high pressure carbamate condenser for subjecting said gas stream to condensation thereby forming a first carbamate-containing solution and releasing heat of condensation, wherein the high pressure carbamate condenser has a connection for supplying carbamate-containing solution to the high pressure reaction zone,
- C) a low pressure decomposer, wherein the low pressure decomposer is configured for subjecting said second urea solution to low pressure decomposition, or wherein the low pressure decomposer is configured for subjecting the processed second urea solution to low pressure carbamate decomposition and wherein the existing plant is configured for first processing said second urea solution at medium pressure in a medium pressure section to give said processed second urea solution, wherein said low pressure carbamate decomposition involves heating in the second urea solution containing carbamate using said heat of condensation from the high pressure carbamate condenser to decompose carbamate, thereby giving a first vapor and a third urea solution also containing carbamate, and
- D) an existing low pressure carbamate condenser configured for subjecting first vapor to condensation,
wherein the method comprises:
    adding an expansion system for expanding the third urea solution to a sub-atmospheric pressure thereby obtaining an expanded third urea solution if the existing plant does not comprise such an expansion vessel,
    adding a unit comprising a first low pressure carbamate condenser and a sub-atmospheric decomposer,
- D1) wherein the first low pressure carbamate condenser is configured for subjecting said first vapor to condensation thereby obtaining a second carbamate-containing solution and second vapor and releasing additional heat of condensation, wherein the first low pressure carbamate condenser has an outlet for transport of the second carbamate-containing solution to the high pressure reaction zone,
- D2) wherein the sub-atmospheric decomposer is configured for subjecting said expanded third urea solution to decomposition of carbamate in using said additional heat of condensation from said first low pressure carbamate condenser by heat transfer through a heat-exchanging wall between said first low pressure carbamate condenser and said sub-atmospheric decomposer, thereby obtaining a fourth urea solution and a third vapor,
    optionally modifying the existing low pressure carbamate condenser into a second low pressure carbamate condenser, having an inlet for said second vapor and configured for second vapor condensation in indirect heat exchange with cooling fluid, thereby obtaining a third carbamate-containing solution, and having an outlet for transport of the third carbamate-containing solution to the high pressure reaction zone, and
    adding a sub-atmospheric carbamate condenser configured for subjecting said third vapor to condensation in indirect heat exchange with cooling fluid, thereby obtaining a fourth carbamate-containing solution, and having an outlet for transport of part or all of the fourth carbamate-containing solution to the high pressure reaction zone, wherein the modified plant is preferably suitable for the urea production process of claim 1.

* * * * *